United States Patent
Richter et al.

(10) Patent No.: US 12,135,322 B2
(45) Date of Patent: Nov. 5, 2024

(54) IN-VITRO METHOD FOR DETERMINING A CELL TYPE OF A WHITE BLOOD CELL WITHOUT LABELING

(71) Applicant: Siemens Healthcare GmbH, Erlangen (DE)

(72) Inventors: Lukas Richter, Hirschaid (DE); Oliver Hayden, Moosburg (DE); Matthias Ugele, Landshut (DE); Markus Weniger, Nuremberg (DE); Oliver Schmidt, Erlangen (DE); Manfred Stanzel, Berching (DE)

(73) Assignee: Siemens Healthineers AG, Erlangen (DE)

( * ) Notice: Subject to any disclaimer, the term of this patent is extended or adjusted under 35 U.S.C. 154(b) by 1049 days.

(21) Appl. No.: 16/980,835

(22) PCT Filed: Mar. 11, 2019

(86) PCT No.: PCT/EP2019/055965
§ 371 (c)(1),
(2) Date: Sep. 14, 2020

(87) PCT Pub. No.: WO2019/175082
PCT Pub. Date: Sep. 19, 2019

(65) Prior Publication Data
US 2021/0365667 A1  Nov. 25, 2021

(30) Foreign Application Priority Data
Mar. 15, 2018 (EP) .................................. 18162033

(51) Int. Cl.
| | |
|---|---|
| *G06T 7/00* | (2017.01) |
| *G01N 33/49* | (2006.01) |
| *G03H 1/00* | (2006.01) |
| *G03H 1/04* | (2006.01) |
| *G06F 18/2135* | (2023.01) |
| *G06T 7/62* | (2017.01) |
| *G06T 7/64* | (2017.01) |
| *G06T 7/66* | (2017.01) |
| *G06V 10/77* | (2022.01) |
| *G06V 20/69* | (2022.01) |
| *G06V 20/80* | (2022.01) |

(52) U.S. Cl.
CPC ........... *G01N 33/49* (2013.01); *G03H 1/0005* (2013.01); *G03H 1/0443* (2013.01); *G06F 18/2135* (2023.01); *G06T 7/0012* (2013.01); *G06T 7/62* (2017.01); *G06T 7/64* (2017.01); *G06T 7/66* (2017.01); *G06V 10/7715* (2022.01); *G06V 20/693* (2022.01); *G06V 20/698* (2022.01); *G03H 2001/005* (2013.01); *G03H 2210/55* (2013.01); *G06T 2207/10056* (2013.01); *G06T 2207/30024* (2013.01); *G06V 2201/03* (2022.01)

(58) Field of Classification Search
CPC ... G06T 7/62; G06T 7/64; G06T 2207/10056; G06T 2207/30024; G06T 7/0012; G06V 2201/03; G03H 2001/005
See application file for complete search history.

(56) References Cited

U.S. PATENT DOCUMENTS

| | | | |
|---|---|---|---|
| 2017/0219568 A1 | 8/2017 | Schütze et al. | |
| 2021/0303818 A1* | 9/2021 | Randolph | .............. G06N 3/045 |

FOREIGN PATENT DOCUMENTS

| | | |
|---|---|---|
| CN | 101389959 A | 3/2009 |
| CN | 103398935 B | 6/2015 |
| CN | 103471982 B | 11/2015 |
| CN | 103745210 B | 2/2018 |
| CN | 105659068 B | 4/2019 |
| EP | 3220130 A1 | 9/2017 |
| JP | H06505099 A | 6/1994 |
| JP | 2009539097 A | 11/2009 |
| JP | 2014502720 A | 2/2014 |
| JP | 2016511397 A | 4/2016 |
| WO | WO2015195609 A1 | 12/2015 |

OTHER PUBLICATIONS

Tabrizi, P. R. et al.: "Using PCA and LVQ Neural Network for Automatic Recognition of Five Types of White Blood Cells", 2010 Annual International Conference of the IEEE Engineering In Medicine And Biology Society: (EMBC 2010), Aug. 31, 2010 (Aug. 31, 2010), Seiten 5593-5596, XP032108742, IEEE, Piscataway, NJ, USA DOI: 10.1109/IEMBS.2010.5626788 ISBN: 978-1-4244-4123-5.
Robison, C.J. et al.: "Imaging White Blood Cells using a Snapshot Hyper-Spectral Imaging System" (2016). Graduate Theses, Dissertations, and Problem Reports. 6519. https://researchrepository.wvu.edu/etd/6519; 2016.
Huang, Der-Chen et al.: "A computer assisted method for leukocyte nucleus segmentation and recognition in blood smear images", Journal of Systems and Software, vol. 85, No. 9, pp. 2104-2118, XP028499919, Elsevier North Holland, New York, NY, US ISSN: 0164-1212, DOI: 10.1016/J.JSS.2012.04.012; [found on Apr. 18, 2012] Point 1., 3.1., 3.3., 3.4., 5.4., 6., figures 2,3; tables 2,4; abstract; 2012.

(Continued)

*Primary Examiner* — Maryam Monshipouri
(74) *Attorney, Agent, or Firm* — Dugan & Dugan, PC (57) ABSTRACT

An in-vitro method for determining a cell type of a white blood cell in a biological sample does so without labeling, wherein a microscopy apparatus images the cell, and physical parameters of the cell are ascertained from the image of the cell by an automated image analysis. The cell type of the white blood cell is determined on the basis of the physical parameters and on the basis of principal component analysis parameters (PCA parameters), wherein the principal component analysis parameters comprise linear combinations of at least some of the physical parameters.

14 Claims, 3 Drawing Sheets

(56) References Cited

OTHER PUBLICATIONS

Yampri, P. et al.: "White Blood Cell Classification based on the Combination Eigen Cell and Parametric Feature Detection", 2006 1st IEEE Conference on Industrial Electronics and Applications, May 1, 2006 (May 1, 2006), pp. 1-4, XP031026640, Piscataway, NJ : IEEE Service Center, US DOI: 10.1109/ICIEA.2006.257341; ISBN: 978-0-7803-9513-8; the whole document; 2006.
International Search Report and Written Opinion of related International Application No. PCT/EP2019/055965 mailed Jun. 4, 2019.
Extended European Search Report of related Application No. EP18162033.7 mailed Aug. 30, 2018.
Wang Y. et al.: "Application and Analysis in the Biomedicine Field Using Digital Holographic Technology"; Chinese Journal of Lasers; vol. 41, No. 2, Feb. 28, 2014; pp. 1-13 (with English Abstract).

* cited by examiner

IN-VITRO METHOD FOR DETERMINING A CELL TYPE OF A WHITE BLOOD CELL WITHOUT LABELING

CROSS REFERENCE TO RELATED APPLICATIONS

This is a 371 of PCT/EP2019/055965, filed Mar. 11, 2019, which claims priority to European Patent Application No. EP 18162033.7, filed Mar. 15, 2018, both of which are hereby incorporated by reference herein in their entireties for all purposes.

FIELD

The invention relates to an in-vitro method for determining a cell type of a white blood cell in a biological sample without labeling by using a microscopy apparatus.

BACKGROUND

Determining cells and assigning these to a cell type is very important in cytology. In a hematological examination, for example, cellular blood components, i.e., erythrocytes, thrombocytes, and white blood cells, are determined and quantified. An ascertainment of the number of leukocytes ("white blood count", WBC) should be able to differentiate the principal populations of the white blood cells for comprehensive diagnostics. White cells are differentiated according to granular cells (neutrophils, eosinophils, basophils) and non-granular cells (lymphocytes, monocytes). In addition to granularity, the cells also differ in respect of the fragmentation of the cell nucleus (without fragmentation: mononuclear cells, i.e., lymphocytes and monocytes; polymorphonuclear cells: eosinophils, basophils, and neutrophils) and the cell size. Staining is used for differentiating the granular cells, especially eosinophils and basophils. Cell populations are usually evaluated by fully automated hematology analyzers or by microscopy. Fully automated analyzers must analyze the populations according to set algorithms (with the aid of, e.g., impedance, stray light, and absorption measurements). However, this often leads to error messages being displayed, for example, in the case of pathological samples. Microscopy is usually carried out in the next step as a validation process for the cells incorrectly determined by the hematology analyzer. This step is complicated and costly since it also requires a manual assessment in addition to sample preparation, microscopy, and further work to be carried out manually.

Changes in the blood count are a phenomenon that accompanies many diseases, and so these changes make an important differential-diagnostic contribution. The blood count is one of the most common laboratory examinations and comprises, inter alia, the determination of hemoglobin and the ascertainment of the number of erythrocyte, leukocyte, and thrombocyte cells. The full blood count additionally contains the differential blood count, which also includes leukocyte differentiation.

On account of the processes employed (e.g., Mie scattering), a complicated sample preparation (cells are stained or partially lysed) is necessary, particularly for analyzing white blood cells. However, in the case of pathological blood samples, the sample preparation, such as lysis, is often only implemented insufficiently and so a manual examination of the blood cells is required, e.g., by smearing and staining. However, this process is only qualitative and only has restricted use for uncommon white blood cells on account of the small number of cells counted (approximately 100 to 200 cells per slide). However, for an initial diagnosis of pathological samples such as, e.g., leukemia, blood smears with the subsequent staining of the blood cells is currently the standard process.

Mechanized leukocyte differentiation in whole blood can be implemented, for example, by means of a resistance measurement, conductance measurement, laser stray light measurement, flow cytometry or cytochemical peroxidase reaction. Here, the erythrocytes are initially lysed and the leukocytes are singulated in a flow cell.

By way of example, in order to carry out quantitative blood cell diagnostics, it is possible to dispense with a hematology analyzer and instead apply microscopy to each individual cell. This allows quantitative determination of the blood count, independently of set evaluation algorithms and flags. However, a disadvantage of this approach is a lower sample throughput than in the case of a hematology analyzer and the still existing outlay relating to immobilizing and staining the cells on object carriers. Moreover, these stains only have restricted reproducibility and exhibit great dependence on humidity, staining duration, temperature and more. A disadvantage in pure microscopy in comparison with flow cytometers used in hematology analyzers lies in quantifying the cell volumes.

To create a manual blood count, use is made of specific staining techniques designed for the analysis of whole blood, such as, e.g., Wright-Giemsa staining. To this end, whole blood is smeared on an object carrier and counted to create a differential blood count, for example, to approximately 100 leukocytes, in difficult cases to approximately 3-times 100 cells where necessary.

A blood smear with subsequent staining of the blood cells is the standard process for the initial diagnosis of pathological samples. In the case of leukemia, a distinction can be drawn between "acute myeloid leukemia (AML)," "acute lymphoblastic leukemia (ALL)," "chronic myeloid leukemia (CML)," and "chronic lymphocytic leukemia (CLL)" types on the basis of the differential blood count by way of characteristically occurring cell populations.

On account of the small statistics in the case of blood smears (approximately 100 to 200 cells per slide), flow cytometry is used, as a rule, for verifying the diagnosis and for more accurate determination of subtypes of leukemia. In the process, the white blood cells are labeled with specific (fluorescence) antibodies and the differentiation is implemented by the characteristic expression patterns, which are reflected in the scattered image. Additionally, bone marrow punctures may be required for an accurate diagnosis in complicated cases.

The use of dyes for differentiating between different (blood) cells was already developed in the 1860s. Gustav Giemsa developed the staining method named in his honor, originally for rendering malaria parasites visible and subsequently modified for staining *Treponema pallidum*, the cause of syphilis. Wright-Giemsa staining, currently used, allows white blood cells to be distinguished and therefore represents the initial diagnosis for leukemic diseases.

For accurately determining the leukemia immunophenotype, flow cytometry (fluorescence-activated cell sorting, FACS) is used as a standard. Here, a multiplicity of different (fluorescence) antibodies are used; both peripheral blood and bone marrow samples are used as samples. Evaluation is implemented by means of specific programs for analyzing FACS data (e.g., Kaluza). Here, it is possible to distinguish between different clinical pictures by the presence of data points in previously set regions, which are also referred to as "gates." Distinguishing between the four aforementioned forms of leukemia without staining/labeling by using a purely microscopic process is unknown to date.

U.S. Pat. No. 8,406,498 has disclosed an imaging flow cytometer, by means of which the differentiation of white blood cells can be determined directly. However, staining is also used in this case, in particular in order to distinguish between eosinophils and basophils. Consequently, the aforementioned disadvantages also arise here.

SUMMARY OF THE INVENTION

Consequently, the object of the invention is that of providing a more efficient and robust method for differentiating white blood cells which, in particular, does not require staining and/or labeling of the blood cells.

The object is achieved by the method according to the invention, the cell analysis device according to the invention, and the microscopy apparatus according to the independent patent claims. Advantageous developments of the invention are specified by the dependent claims.

The in-vitro method according to the invention for determining a cell type of a blood cell in a biological sample without labeling is carried out with the aid of a microscopy apparatus and a cell analysis device. Here, a microscopy apparatus is an appliance that allows very small objects to be observed under great magnification and comprises, e.g., a light microscope, a scanning electron microscope, a phase contrast microscope, a digital holographic microscope, or a microscope with an ultrasonic sensor (e.g., an acoustic microscope). In the process, the microscopy apparatus images the cell. Physical parameters of the cell are ascertained from the image representation of the cell by means of an automated image analysis.

The cell analysis device, i.e., an appliance or appliance component suitable for electronic data processing and configured for ascertaining physical parameters of the cell from the image representation of the cell by means of an automated image analysis, carries out a method according to the invention, as described in more detail below.

The subject matter of the invention relates to an in-vitro method for determining a cell type of a white blood cell in a biological sample without labeling, wherein a microscopy apparatus images the cell and physical parameters of the cell are ascertained from the image representation of the cell by means of an automated image analysis, wherein the cell type of the white blood cell is determined on the basis of the physical parameters and on the basis of principal component analysis parameters (PCA parameters), wherein the principal component analysis parameters comprise linear combinations of at least some of the physical parameters.

Preferably, the cell type of the white blood cell is determined on the basis of predetermined criteria in respect of the physical parameters and the principal component analysis parameters (PCA parameters), wherein the corresponding cell type is present if the respective predetermined criteria are satisfied.

The phrase "predetermined criteria" relates to a criterion or a plurality of criteria which are determined on account of one or more physical and/or principal component analysis parameters (PCA parameters). Here, the respective criterion is preferably determined on the basis of a comparison between the corresponding image representations of various white blood cell types to be distinguished.

On account of the dispensing with a staining method, the method allows a high sample throughput and a qualitative and/or quantitative determination of cells. This facilitates a microscopy process with a high sample throughput, and it is possible to dispense with conventional hematology analyzers.

Preferably, the determined cell type of the white blood cell is one of the following principal types of white blood cells from the group comprising monocytes, neutrophils, basophils, eosinophils, and lymphocytes.

In a further preferred embodiment of the method according to the invention, the determined cell type is one of the principal types of white blood cells and/or a sub-type of white blood cells from the group comprising myelocytes, metamyelocytes, promyelocytes, blasts, megakaryocytes, plasma cells, atypical lymphocytes, and Sézary cells.

In a further preferred embodiment, the determination of the respective cell type of a multiplicity of white blood cells in a sample is used to characterize the respective cell populations and the present cell populations are used to determine whether acute myeloid leukemia (AML), acute lymphoblastic leukemia (ALL), chronic myeloid leukemia (CML), or chronic lymphocytic leukemia (CLL) is present in the patient from whom the sample originated.

Preferably, the physical parameters of the cell comprise parameters from the following group, which comprises area covered by the cell (cellArea), perimeter of the cell (perimeter), width of the cell (width), height of the cell (height), ratio of the width to the height of the cell (aspectRatio), similarity of the geometric shape of the cell to a circle (circularity), mean radius of the cell (radiusMean), variance of the radius of the cell (radiusVariance), degree of coverage of the cell (solidity), equivalent diameter corresponding to the covered area of the cell (equivalentDiameter), optical volume of the cell (opticalVolume), maximum optical height of the cell (opticalHeightMaximum), minimum optical height of the cell (opticalHeightMinimum), mean optical height of the cell (opticalHeightMean), variance of the optical height of the cell (opticalHeightVariance), biconcavity of the cell (biconcavity), sphericity of the cell (sphericity), shift of the center of mass of the cell (massCenterShift), contrast of the cell (contrast), dissimilarity of the cell (dissimilarity), homogeneity of the cell (homogeneity), energy of the cell (energy), entropy of the cell (entropy).

Preferably, the physical parameters of the cell are defined as set forth below.

| Expression | Unit | Definition/notes |
| --- | --- | --- |
| cellArea | $\mu m^2$ | Contour area |
| perimeter | $\mu m$ | Contour perimeter |
| width | $\mu m$ | Width of rotated bounding rectangle with minimum area |
| height | $\mu m$ | Height of rotated bounding rectangle with minimum area |
| aspectRatio | | max(width, height)/min(width, height); |
| circularity | [0, 1] | $4\pi$*cellArea/perimeter2. Circularity of a circle is 1. The closer it gets to 0, the less circular the contour is. |
| radiusMean | $\mu m$ | The mean distance between the centroid of the contour and each contour support point. Centroid is calculated out of contour moments. Please note that for contours defined by only a few points this does not match the radius for each contour pixel, but only for the supporting points (e.g., a rectangle can be defined by four supporting points), speeding up computation. |

| Expression | Unit | Definition/notes |
|---|---|---|
| radiusVariance | | The variance of the distance between the centroid of the contour and each contour support point. |
| solidity | | Solidity is the ratio of contour area to its convex hull area. First, the convex hull of the contour is calculated. The solidity is calculated by cellArea/convex hull area. Solidity grows for irregular shaped objects. |
| equivalentDiameter | μm | Equivalent Diameter is the diameter of the circle whose area is same as the contour area. Calculated by sqrt((4*cellArea)/n). |
| opticalVolume | μm$^3$ | The volume of a single pixel can be calculated by phase value*0.53(wavelength)/(2n)*0.345(pixel size). The overall optical volume is the sum of all contour volume pixels. |
| opticalHeightMaximum | | The maximum phase value inside the contour |
| opticalHeightMinimum | | The minimum phase value inside the contour. |
| opticalHeightMean | | The mean phase value inside the contour. |
| opticalHeightVariance | | The phase value variance inside the contour. |
| biconcavity | [−1, 1] | Extracts pixel phase values of a horizontal and vertical cut through the middle of the contours bounding rectangle. Checks correlation of pixel values with the polynomial −4*x^4 + 4*x^2 + 0.5 scaled to the same length. Return minimum value of the two cuts. |
| sphericity | [−1, 1] | Extracts pixel phase values of a horizontal and vertical cut through the middle of the contours bounding rectangle. Checks correlation of pixel values with the polynomial −x^2 + 1 scaled to the same length. Return minimum value of the two cuts. |
| massCenterShift | | Euclidian distance between geometric centroid and mass centroid. Mass centroid is calculated out of the squared phase values. Values for X and Y are calculated by getting the ID mass center along each axis. Axis mass center is calculated by (e.g. for x axis) mc = 1/(m1 + . . . + mn) * (x1*m1 + . . . + xm*mn) with the m1 . . . mn the summed-up phase values for each x value. |
| contrast | | 5 features are extracted out of the gray level co-occurrence matrix. To speed up the process, the gray values are scaled by ¼ before constructing the matrix (resulting in only 64 possible values). Contrast or local intensity variation will favor contributions from P(i, j) away from the diagonal. |
| dissimilarity | | Dissimilarity measure based on GLCM of phase values converted to 6 bit grayscale image for the pixels inside cell contour. |
| homogeneity | | homogeneous scene will contain only a few gray levels, giving a GLCM with only a few but relatively high values of P(i, j) |
| energy | | Measures order. |
| entropy | | Measures disorder. |

Details to the definition of contrast and the 5 features which are extracted out of the gray level co-occurrence matrix can be found in "GLCM Texture: A Tutorial v. 3.0 March 2017" at the webpages of the University of Calgary.

In further preferred embodiments, additional information that is additionally available depending on the microscopy method can be captured. By way of example, the intensity distribution, a polarization contrast, or fluorescence contrast can be additionally used to facilitate better differentiation.

Preferably, the principal component analysis parameters (PCA parameters) comprise one, two, three, four, or five different linear combinations of parameters.

Preferably, the principal component analysis parameters (PCA parameters) comprise linear combinations of the parameters set forth below.

At least one PCA parameter preferably comprises a linear combination of the parameters cellArea, perimeter, width, height, aspectRatio, circularity, radiusMean, radiusVariance, solidity, equivalentDiameter, opticalVolume, opticalHeightMaximum, opticalHeightMinimum, opticalHeightMean, opticalHeightVariance, biconcavity, sphericity, massCenterShift, contrast, dissimilarity, homogeneity, energy, entropy.

In particular, the PCA parameters comprise a total of six PCA parameters, with each of the PCA parameters respectively preferably comprising a linear combination of the parameters cellArea, perimeter, width, height, aspectRatio, circularity, radiusMean, radiusVariance, solidity, equivalentDiameter, opticalVolume, opticalHeightMaximum, opticalHeightMinimum, opticalHeightMean, opticalHeightVariance, biconcavity, sphericity, massCenterShift, contrast, dissimilarity, homogeneity, energy, and entropy.

Preferably, the principal component analysis parameters (PCA parameters) comprise the following parameters Val1 to Val6.

$$Val1 = -0.2514235930087 *$$
$$((cell.cellArea - (42.9755016744))/10.5788867263146) +$$
$$-0.249974748498971 *$$
$$((cell.perimeter - (24.576753500494))/3.20109088487221) +$$
$$-0.237593744589169 *$$
$$((cell.width - (7.35723468359436))/1.00790834623485) +$$
$$-0.241385243730167 *$$
$$((cell.height - (7.28724864632538))/1.00167379952967) +$$
$$0.0500690750767191 *$$
$$((cell.aspectRatio - (1.0727084035923))/0.0503940328943091) +$$
$$-0.0325934362800635 *$$
$$((cell.circularity - (0.879203898319695))/0.0171374141190303) +$$
$$-0.251748682215606 *$$

$((cell.radiusMean - (3.67481430203961))/0.47807494523509) + -0.0358686373697572 *$ $((cell.radiusVariance - (0.534334347573423))/ 0.135861132157575) + -0.0713429028935052 *$ $((cell.solidity - (0.973653367948167))/0.00642977966295229) + -0.251801959117612 *$ $((cell.equivalentDiameter - (7.33498993492049))/ 0.957125629695256) + -0.271859966910455 *$ $((cell.opticalVolume - (10.9434893272532))/4.39789306763487) + -0.264893256207984 *$ $((cell.opticalHeightMaximum - (4.0508608252182))/ 1.13386516864492) + -0.019499726282544 *$ $((cell.opticalHeightMinimum - (0.917628988325119))/ 0.00943812184922224) + -0.263403666244868 *$ $((cell.opticalHeightMean - (2.56913326007255))/ 0.578640046049587) + -0.264398202286343 *$ $((cell.opticalHeightVariance - (0.891494679587935)) 0.319599313085186) + 0.0683113521964872 *$ $((cell.biconcavity - (-0.1590427888386))/0.0878662330982137) + 0.0532706264409643 *$ $((cell.sphericity - (0.952179340809924))/0.0556215659482945) + -0.13507569551957 *$ $((cell.massCenterShift - (0.321787377964238))/ 0.279787203971966) + -0.2377555890641 *$ $((cell.contrast - (5.99415440523299))/3.28737834908757) + -0.245223436384692 *$ $((cell.dissimilarity - (1.8261947255628))/0.524533027046986) + 0.241198017846531 *$ $((cell.homogenity - (0.421196396914475))/0.0787508131258171) + 0.258958179846163 *$ $((cell.energy - (0.106234099933335))/0.0303777835437848) + -0.267352762571249 *$ $((cell.entropy - (4.85017551257248))/0.552270252441689) + 0;$ $Val2 = -0.168670616411677 *$ $((cell.cellArea - (24.975016744))/10.5788867263146) + -0205776175336618 *$ $((cell.perimeter - (24.576753500494))/3.20109088487221) + -0.186558934231474 *$ $((cell.width - (7.35723468359436))/1.00790834623485) + -0.183141003655306 *$ $((cell.height - (7.28724864632538))/1.00167379952967) + -0.0928942621464152 *$ $((cell.aspectRatio - (1.0727084035923))/0.0503940328943091) + 0.505899790631485 *$ $((cell.circularity - (0.879203898319695))/0.0171374141190303) + -0.169985535864666 *$ $((cell.radiusMean - (3.67481430203961))/0.4780749523509) + -0.377167185427535 *$ $((cell.radiusVariance - (0.534334347573423))/ 0.135861132157575) + 0.416007969970529 *$ $((cell.solidity - (0.973653367948167))/0.00642977966295229) + -0.166991998607427 *$ $((cell.equivalentDiameter - (7.33498993492049))/ 0.957125629695256) + -0.00731744872935898 *$ $((cell.opticalVolume - (10.9434893272532))/4.39789306763487) + 0.106456651440064 *$ $((cell.opticalHeightMaximum - (4.0508608252182))/ 1.13386516864492) + 0.20085391219078 *$ $((cell.opticalHeightMinimum - (0.917628988325119))/ 0.00943812184922224) + 0.122345079558179 *$ $((cell.opticalHeightMean - (2.56913326007255))/ 0.578640046049587) + 0.101062869417052 *$ $((cell.opticalHeightVariance - (0.891494679587935))/ 0.319599313085186) + 0.217089205338001 *$ $((cell.biconcavity - (-0.1590427888386))/0.0878662330982137) + -0.0619295694253695 *$ $((cell.sphericity - (0.952179340809924))/0.0556215659482945) + 0.015656887744252 * ((cell.massCenterShift - (0.321787377964238))/ 0.279787203971966) + 0.198114038338057 *$ $((cell.contrast - (5.99415440523299))/3.28737834908757) + 0.180425506176449 *$ $((cell.dissimilarity - (1.8261947255628))/0.524533027046986) + -0.135400526577736 * ((cell.homogeneity - (0.421196396914475))/ 0.0787508131258171) + -0.0267942709719767 *$ $((cell.energy - (0.106234099933335))/0.0303777835437848) + 0.0722804026404807 *$ $((cell.entropy - (4.85017551257148))/0.552270252441689) + 0;$ $Val3 = -0.152245658792807 *$ $((cell.cellArea - (42.9755016744))/10.5788867263146) + -0.137744345235438 *$ $((cell.perimeter - (24.576753500494))/3.20109088487221) + -0.139046382561896 *$ $((cell.width - (7.35723468359436))/1.00790834623485) + -0.136640064377995 *$ $((cell.height - (7.28724864632538))/1.00167379952967) + 0.143071973661924 *$ $((cell.aspectRatio - (1.0727084035923))/0.0503940328943091) + -0.311832846414789 *$ -continued $$((cell.circularity - (0.879203898319695))/0.0171374141190303) + -0.158405722299146 *$$
$$((cell.radiusMean - (3.67481430203961))/0.47807494523509) + 0.2147365796495 * ((cell.radiusVariance - (0.534334347573423))/0.135861132157575) + -0.290348831318269 *$$
$$((cell.solidity - (0.9733653367948167))/0.00642977966295229) + -0.160436060932553 *$$
$$((cell.equivalentDiameter - (7.33498993492049))/0.957125629695256) + -0.0283231756716574 *$$
$$((cell.opticalVolume - (10.9434893272532))/4.39789306763487) + 0.108904826169979 *$$
$$((call.opticalHeightMaximum - (4.0508608252182))/1.13386516864492) + -0.0541041915771913 *$$
$$((cell.opticalHeightMinimum - (0.917628988325119))/0.00943812184922224) + 0.0482898928982701 *$$
$$((cell.opticalHeightMean - (2.56913326007255))/0.578640046049587) + 0.0740565216581285 *$$
$$((cell.opticalHeightVariance - (0.891494679587935))/0.319599313085186) + 0.33268062359036 *$$
$$((cell.biconcavity - (-0.1590427888386))/0.0878662330982137) + -0.486496428597712 *$$
$$((cell.sphericity - (0.952179340809924))/0.0556215659482945) + 0.404071847572092 * ((cell.massCenterShift - (0.321787377964238))/0.279787203971966) + 0.20021434612418 *$$
$$((cell.contrast - (5.99415110523299))/3.2873783498757) + 0.168546834749071 *$$
$$((cell.dissimilarity - (1.8261947255628))/0.524533027046986) + -0.114748435539571 * ((cell.homogeneity - (0.421196396914475))/0.0787508131258171) + -0.0143576741936659 *$$
$$((cell.energy - (0.1062340999933335))/0.0303777835437848) + 0.070606562249387 *$$
$$((cell.entropy - (4.85017551257248))/0.552270252441689) + 0;$$
$$Val4 = -0.261610677611746 *$$
$$((cell.cellArea - (29.4395201580311))/5.11005121908855) + -0.261094203446583 *$$
$$((cell.perimeter - (20.4714469010994))/1.7376311988654) + -0.22286167654857 *$$
$$((cell.width - (6.12959751130435))/0.59548518687133) + -0.229916753106545 *$$
$$((cell.height - (6.05150421944159))/0.591609173525849) + 0.011807520590896 *$$
$$((cell.aspectRatio - (1.0869912949338))/0.0546526376570488) + 0.0262225683553752 *$$

-continued $$((cell.circularity - (0.876941946272043))/0.0179521439605036) + -0.261160667395425 *$$
$$((cell.radiusMean - (3.05876819557268))/0.255900843697689) + -0.0941868494695694 *$$
$$((cell.radiusVariance - (0.516064433989357))/0.111459058693624) + -0.110718002570505 *$$
$$((cell.solidity - (0.971597800798176))/0.00720404258117219) + -0.20831711849364 *$$
$$((cell.equivalentDiameter - (6.10101233363755))/0.511139800830794) + -0.283417789826245 *$$
$$((cell.opticalVolume - (5.49637143295321))/1.39356683120867) + -0.28041071625337 *$$
$$((cell.opticalHeightMaximum - (2.78997632108204)0/0.357459556742829) + 0.00345191681990364 *$$
$$((cell.opticalHeightMinimum - (0.916982544759395))/0.0114607243403515) + -0.267687084654929 *$$
$$((cell.opticalHeightMean - (1.90610826785609))/0.176319079561605) + -0.279754464234688 *$$
$$((cell.opticalHeightVariance - (0.531938907690763))/0.107019179729975) + 0.121035300134979 *$$
$$((cell.biconcavity - (-0.11874291555068))/0.0878957408234967) + -0.0161513556541555 *$$
$$((cell.sphericity - (0.955634909899621))/0.04264168644697) + -0.107830413342139 *$$
$$((cell.massCenterShift - (0.205413097350611))/0.143266493406051) + -0.216912000881217 *$$
$$((cell.contrast - (2.94739193186445))/0.851979848483421) + -0.233161325461211 * ((cell.dissimilarity - (1.31231869619681))/0.185666125635144) + 0.222121616068744 * ((cell.homogeneity - (0.499177299392145))/0.043929343763229) + 0.237462579736086 * ((cell.energy - (0.141919956703913))/0.0213959679195142) + -0.268766115142943 * ((cell.entropy - (4.20317134129727))/0.263391474017291) + 0;$$
$$Val5 = 0.277185206648515 * ((cell.cellArea - (29.4395201580311))/5.11005121908855) + 0.289025861167001 * ((cell.perimeter - (20.4714469010994))/1.73763119886254) + 0.27869771372156 *$$
$$((cell.width - (6.12959751130435))/0.59548518687133) + 0.226791977731385 *$$
$$((cell.height - (6.05150421944159))/0.591609173525849) + -0.0154016557869195 *$$

$$((cell.aspectRatio - (1.0869912949228))/$$
$$0.0546526376570488) + -0.104962015198417 *$$
$$((cell.circularity - (0.876941946272043))/$$
$$0.0179521439605036) + 0.280118171306254 *$$
$$((cell.radiusMean - (3.05876819557268))/$$
$$0.255900843697689) + 0.122071737825644 *$$
$$((cell.radiusVariance - (0.516064433989357))/$$
$$0.111459058693624) + -0.0757806415365649 *$$
$$((cell.solidity - (0.971597800798176))/$$
$$0.00720404258117219) + 0.279776181994244 *$$
$$((cell.equivalentDiameter - (6.10101233363755)/$$
$$0.511139800830794) + 0.1270079667257615 *$$
$$((cell.opticalVolume - (5.49637143295321))/$$
$$1.39356683120867) + -0.166674686515488 *$$
$$((cell.opticalHeightMaximum - (2.78997632108204))/$$
$$0.3574595556742829) + -0.0801206102287044 *$$
$$((cell.opticalHeightMinimum - (0.916982544759395))/$$
$$0.011460724340515) + -0.13904585273397 *$$
$$((cell.opticalHeightMean - (1.90610826785609))/$$
$$0.176319079561605) + -0.157320201651437 *$$
$$((cell.opticalHeightVariance - (0.531938907690763))/$$
$$0.107019179729975) + -0.0137496049824385 *$$
$$((cell.biconcavity - (-0.11874291555068))/$$
$$0.0878957408234967) + -0.0124754663656207 *$$
$$((cell.sphericity - (0.955634909899621))/$$
$$0.04264168644697) + -0.00354707655665248 *$$
$$((cell.massCenterShift - (0.205413097350611))/$$
$$0.143266493406051) + -0.337317104471527 *$$
$$((cell.contrast - (2.94739193186445))/$$
$$0.85297848483421) + -0.351605489070963 *$$
$$((cell.dissimilarity - (1.3123186961681))/$$
$$0.185666125635144) + 0.324115001671015 *$$
$$((cell.homogeneity - (0.499177299392145))/$$
$$0.043929343763229) + 0.20286086484872 *$$
$$((cell.energy - (0.141919956703913))/$$
$$0.0213959679195142) + -0.208528317348662 *$$
$$((cell.entropy - (4.20317134129727))/$$
$$0.263391471017291) + 0;$$
$$Val6 = -0.0822117013411024 * ((cell.cellArea - (29.4395201580311))/$$
$$5.11005121908855) + -0.0136983441801879 *$$
$$((cell.perimeter - (20.4714469010994))/$$
$$1.73763119886254) + -0.0421965767155267 *$$
$$((cell.width - (6.12959751130435))/$$
$$0.59548518687133) + -0.0105097694902179 *$$

$$((cell.height - (6.05150421944159))/$$
$$0.59609173525849) + 0.0829553453256781 *$$
$$((cell.aspectRatio - (1.0869912949338))/$$
$$0.0546526376570488) + -0.601802580015178 *$$
$$((cell.circularity - (0.876941946272043))/$$
$$0.0179521439605036) + -0.0832961277585592 *$$
$$((cell.radiusMean - (3.05876819557268))/$$
$$0.255900843697689) + 0.312125036264253 *$$
$$((cell.radiusVariance - (0.516064433989357))/$$
$$0.111459058693624) + -0.548644911166917 *$$
$$((cell.solidity - (0.971597800798176))/$$
$$0.00720404258117219) +$$
$$-0.0887226111099722 *$$
$$((cell.equivalentDiameter - (6.10101233363755))/$$
$$0.511139800830794) + -0.065558074724381 *$$
$$((cell.opticalVolume - (5.49637143295321))/$$
$$1.39365583120867) +$$
$$0.00635200779277076 * ((cell.opticalHeightMaximum -$$
$$(2.78997632108204))/0.357459555674 2829) +$$
$$-0.20824275146043 * ((cell.opticalHeightMinimum -$$
$$(0.916982544759395))/$$
$$0.0114607243403515) + -0.052855467177894 *$$
$$((cell.opticalHeightMean - (1.90610826785609))/$$
$$0.176319079561605) +$$
$$0.0139425503541623 * ((cell.opticalHeightVariance -$$
$$(0.531938907690763))/$$
$$0.107019179729975) + 0.0212708260463394 *$$
$$((cell.bivonvacity - (-0.11874291555068))/$$
$$0.0878957408234957) + -0.281890905467496 *$$
$$((cell.sphericity - (0.955634909899621))/$$
$$0.04264168644697) + 0.258391327626016 *$$
$$((cell.massCenterShift - (0.205413097350611))/$$
$$0.143266493406051) + 0.0744517932956948 *$$
$$((cell.contrast - (2.94739193186445))/$$
$$0.852979848483421) + 0.0587637354201565 *$$
$$((cell.dissimilarity - (1.31231869619681))/$$
$$0.185666125635144) + -0.0404667518409852 *$$
$$((cell.homogeneity - (0.499177299392145))/$$
$$0.043929343763229) + -0.0159289744001 *$$
$$((cell.enegry - (0.141919956703913))/$$
$$0.0213959679195142) + 0.0247292136860108 *$$
$$((cell.entropy - (4.20317134129727))/$$
$$0.263391471017291) + 0;$$

Preferably, imaging the cell comprises overlaying a reference wave on an object wave, recording a resultant interferogram, and/or a computer-implemented mathematical reconstruction.

Here, the application of digital holographic microscopy is particularly advantageous as it allows quantitative capture of the phase information of an object. According to a further embodiment of the method according to the invention, the image representation of the white blood cell is therefore ascertained by means of digital holographic microscopy, interference phase microscopy, and/or quantitative phase microscopy. These microscopy processes facilitate a particularly high axial resolution, i.e., in the direction of the optical axis of the microscope. Digital holographic microscopy facilitates a resolution of up to 1 nm in the z-direction. This corresponds to a precision that is higher by a factor of 100-1000 than that of other known light-microscopic methods (e.g., confocal microscope). Consequently, a more accurate determination of the cell type is possible on account of the precise ascertainment of the height profile.

Consequently, the microscopy apparatus is preferably a microscope for performing digital holographic microscopy (DHM), interference phase microscopy, or quantitative phase microscopy.

Preferably, the white blood cells are imaged by the microscopy apparatus in a flow cell, wherein the flow cell preferably comprises a channel with a rectangular or square cross-section.

Preferably, the white blood cells are focused by means of laminar sheath flows, preferably by means of four laminar sheath flows.

Preferably, red blood cells are removed from the sample by means of selective lysis before the white blood cells are imaged by means of the microscopy apparatus.

A further advantage is obtained if the method is carried out using one or more non-stained and/or non-desiccated cells. Since the vitality of the cells is not impaired by the method according to the invention, the cells determined by the method can be used further for subsequent analyses after the determination method has been completed.

According to a further exemplary embodiment, the method according to the invention can comprise phenotyping the cell with a label and/or expressing a predetermined receptor for further assigning of the cell. This facilitates a more in-depth molecular biological examination of the determined cell.

The method according to the invention obtains particular relevance, if according to a further embodiment, it is performed using a whole blood sample and/or the biological sample contains blood cells, monocytes, neutrophils, basophils, eosinophils, and/or lymphocytes. This finds predominant use when determining a blood count in hematology.

Further subject matter of the invention relates to a cell analysis device, for example, comprising a microchip or microcontroller, which is configured to carry out one or more of the above-described embodiments of the method according to the invention.

Further subject matter of the invention relates to a microscopy apparatus for determining a cell type of a white blood cell of a biological sample without labeling, comprising a cell analysis device according to the invention.

Preferably, the microscopy apparatus comprises a digital holographic microscope.

According to a further embodiment of the method according to the invention, determining the white blood cell type can comprise determining a cell stage of the cell, in particular for differentiating a cell age, a physiological or morphological state of the cell, or an activity state of the cell. This facilitates recording an image sequence, for example, of activation procedures in a cell.

Digital holographic microscopy (DHM), also referred to as interference phase microscopy, is distinguished by being able to quantitatively capture both intensity and phase of an object in a recording. To this end, it is not an intensity distribution arising by absorption and scattering of light at the object that is recorded, as in conventional microscopy, but a wavefront arising from the superposition of an object wave and a reference wave. From this, the intensity and phase information of the object can be reconstructed with the aid of a computer.

This microscopy process is suitable for examining biological samples as these are substantially transparent to visible light without further sample preparation and therefore have little contrast in a conventional microscope. By recording the phase information, it is possible to very precisely capture the morphology of the cell and to undertake a differentiation of the cell with the aid of this information.

Compared to conventional phase-contrast microscopes, which are usually realized by a phase ring in the objective lens and an annular stop in the condenser, the DHM offers the advantage of being able to determine the phase quantitatively. Accordingly, this is also referred to as quantitative phase contrast microscopy. A reproducible reconstruction of the height profile of the object is only facilitated by quantifying the phase and only this allows an automated determination of the cell type.

It should be noted that the phase shift of the light is determined by the optical path length through the object; refractive index play a role in this case. The refractive index of the sample must be known in order to obtain a true geometric height profile from the phase information. However, in the preferred application of the microscopy of cells, a largely constant and known refractive index can be assumed, as a result of which the phase information can be directly converted into a height profile. Alternatively, the phase information can be recorded at different wavelengths and the influence of the refractive index can be removed by calculation thereby.

It should further be noted that the phase information is only uniquely determined to a phase angle of 360°. By way of example, a measured phase shift of 10° can correspond to a phase shift of 370°, 730°, etc., in reality. Accordingly, the uniqueness range is restricted to the wavelength of the light. In the chosen application of the microscopic observation of cells, this limitation is likewise negligible since biological cells have no steep flanks and hence the phase values of adjacent pixels are available as connection condition. It should further be noted that the phase information is only uniquely determined to a phase angle of 360°. By way of example, a measured phase shift of 10° can correspond to a phase shift of 370°, 730°, etc., in reality. Accordingly, the uniqueness range is restricted to the wavelength of the light. In the chosen application of the microscopic observation of cells, this limitation is likewise negligible since biological cells have no steep flanks and hence the phase values of adjacent pixels are available as connection condition.

The method according to the invention allows a currently applied procedure for creating a differential blood count to be performed without labels. An exemplary procedure for creating a differential blood count comprises, e.g., the ascertainment of a cell size, a maturity state of the cell, i.e., an age of the cell, a Kern plasma relation, the capture of cytoplasmic inclusions and the capture of a chromatin structure.

Interference phase microscopy, also referred to as digital holographic microscopy (DHM), is distinguished in that it can quantitatively capture both an intensity and a phase of an object in a recording. To this end, it is not an image representation of the object that is captured, as in conventional microscopy, but a wavefront which emerges from the superposition of an object wave and a reference wave. From this, intensity and phase information of the object can be reconstructed with the aid of a cell analysis device, for example, a computer.

This microscopy process is suitable for examining biological samples as these are substantially transparent to visible light without further sample preparation and therefore have less contrast in a conventional microscope. By recording the phase information, it is possible to very precisely capture the morphology of the cell and to undertake a differentiation of the cell with the aid of this information.

It is possible to carry out a differentiation of, e.g., white blood cells on the basis of, e.g., reconstructed phase information of a plurality of cells without the cells having to be stained, allowing work to be carried out with fresh, non-desiccated cells. As a result, unnecessary artifacts which arise from various instances of handling of the samples during desiccating and staining are avoided. Here, the images are reproducible and more easily distinguishable by automated computer-assisted image processing. The number of process steps is minimized. This saves costs and time, and reliable and faster diagnostics are facilitated.

In pre-analytics, this allows the use of, e.g., a rounding buffer (i.e., highly diluted SDS buffer solution) to be dispensed with in relation to hematology analyzers. The latter would lead to rounding up of cells which, although suitable for scattered light measurement in the flow cytometer, simultaneously leads to artifacts.

BRIEF DESCRIPTION OF THE DRAWINGS

The invention is once again explained in more detail by specific exemplary embodiments on the basis of the attached drawings. The shown examples represent preferred embodiments of the invention. In detail.

Further.

DETAILED DESCRIPTION OF THE INVENTION

With the aid of the in-vitro method according to the invention, there can be a determination of a cell type of a white blood cell in a biological sample without labeling. In this case, without labeling means that the cells need not be labeled, for example, by fluorescent dyes or radioactive particles. Here, a biological sample may comprise a sample of animal or human blood cells, for example. Preferably, this is a whole blood sample, which, for example, comprises blood cells 10, e.g., leukocytes, eosinophils, or basophils.

In a first experimental example, AML, CML, ALL, CLL and OMF are distinguished on the basis of the respective characteristic scattering patterns.

Figure 4:
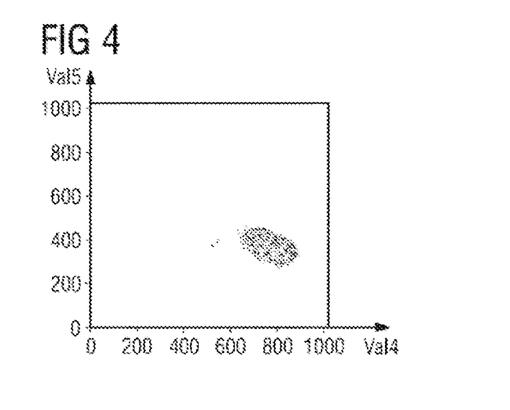
FIG. 4 shows an overview for a CLL sample.
Figure 5:
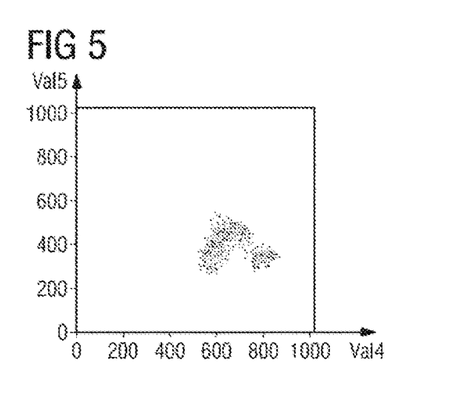
FIG. 5 shows an overview for an OMF sample.
Figure 6:
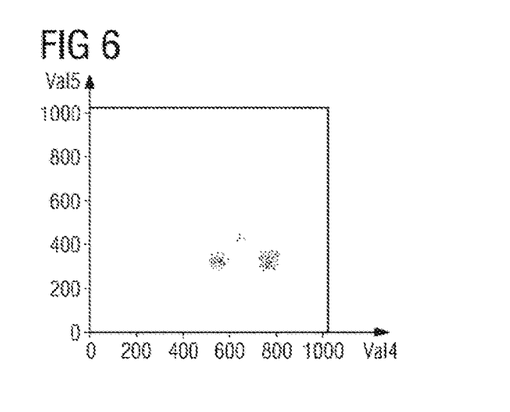
FIG. 6 shows an overview for a healthy sample, with PCA parameters being plotted in each case.

FIG. 1 to FIG. 6 show characteristic scattering patterns of AML (FIG. 1), CML (FIG. 2), AL (FIG. 3), CLL (FIG. 4), OMF (FIG. 5), and a healthy sample (FIG. 6). Here, "OMF" represents osteomyelofibrosis, a sub-type of the group of myeloproliferative neoplasms (MPNs). The PCA parameters Val4 and Val5 (see above for the corresponding linear combination) are used for the distinction.

The distinguishing criteria for the samples of patients with one of the different types of leukemia or of healthy subjects are as follows:

Sample of a healthy subject: three clearly separates data regions:
$1^{st}$ region: Val4=400-650, Val5=200-500,
$2^{nd}$ region: Val4=600-750, Val5=400-600,
$3^{rd}$ region: Val4=700-850, Val5=250-400.

Figure 1:
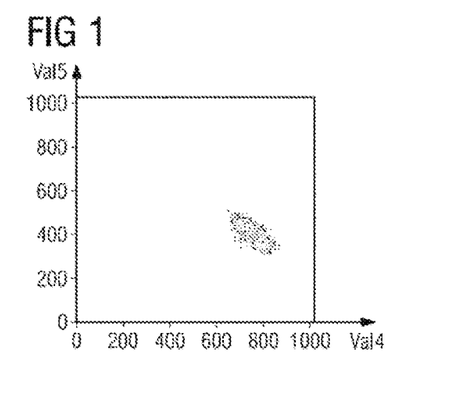
FIG. 1 shows an overview for an AML sample.

Sample of a patient with AML: only one continuous data region:
Val4=600-900, Val5=300-600.

Figure 2:
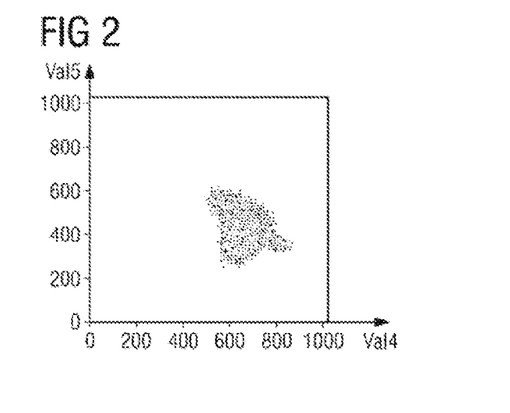
FIG. 2 shows an overview for a CML sample.

Sample of a patient with CML: contiguous data region which can be subdivided into 3 regions:
$1^{st}$ region: small population in the region of Val4=400-550, Val5=200-500,
$2^{nd}$ region: dominant main population in the region of Val4=500-700, Val5=200-500,
$3^{rd}$ region: small population in the region of Val4=700-850, Val5=250-400.

Figure 3:
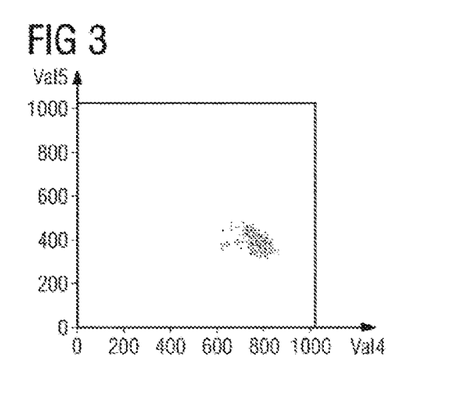
FIG. 3 shows an overview for an ALL sample.

Sample of a patient with ALL: large main population with 2 small secondary populations:
$1^{st}$ region: dominant main population in the region of Val4=700-850, Val5=300-500,
$2^{nd}$ region: small population in the region of Val4=550-700, Val5=300-450,
$3^{rd}$ region: small population in the region of Val4=500-700, Val5=450-600.

Sample of a patient with CLL: large main population with a small secondary population:
$1^{st}$ region: dominant main population in the region of Val4=650-900, Val5=300-500,
$2^{nd}$ region: small population in the region of Val4=400-600, Val5=300-500.

Sample of a patient with OMF: contiguous data region which can be subdivided into 4 regions:
$1^{st}$ region: Val4=700-900, Val5=200-400,
$2^{nd}$ region: Val4=600-750, Val5=400-550,
$3^{rd}$ region: Val4=500-650, Val5=250-450, 4$^{th}$ region: small population in the region of Val4=400-650, Val5=450-700.

In a second experimental example, AML, CML, ALL, CLL and OMF are distinguished on the basis of the respective characteristic scattering patterns.

Figure 10:
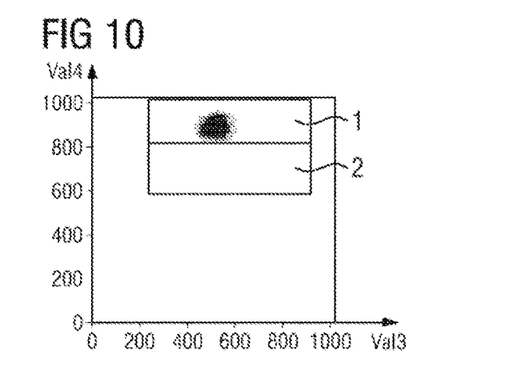
FIG. 10 shows characteristic scattering patterns for myeloblast and lymphoblast gates of a CLL sample.
Figure 11:
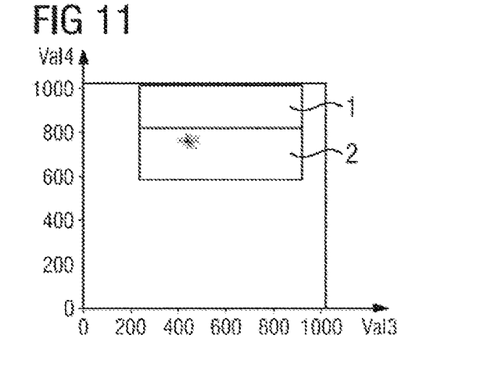
FIG. 11 shows characteristic scattering patterns for myeloblast and lymphoblast gates of an OMF sample.
Figure 12:
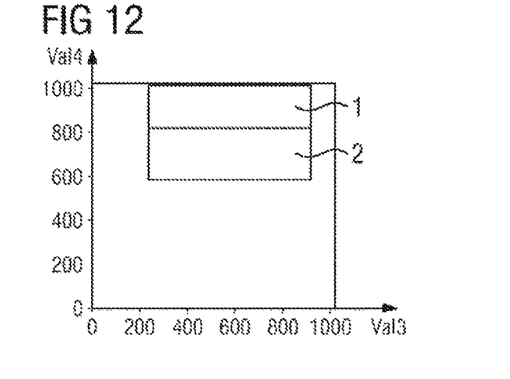
FIG. 12 shows characteristic scattering patterns for myeloblast and lymphoblast gates of a healthy sample, Further.

FIGS. 7 to 12 show characteristic scattering patterns of AML (FIG. 7), CML (FIG. 8), ALL (FIG. 9), CLL (FIG. 10), OMF (FIG. 11), and a healthy sample (FIG. 12). The PCA parameters Val3 and Val4 (see above for the corresponding linear combination) are used for the distinction. Two large regions are defined:

1$^{st}$ region: Val4=235-920, Val5=576-816 (="myeloblasts" gate (2)),

2$^{nd}$ region: Val4=235-920, Val5=816-1015 (="lymphoblasts" gate (1)).

The distinguishing criteria for the samples of patients with one of the different types of leukemia or of healthy subjects are as follows:

Sample of healthy subject: zero or only a very small number of data points in both gates.

Figure 7:
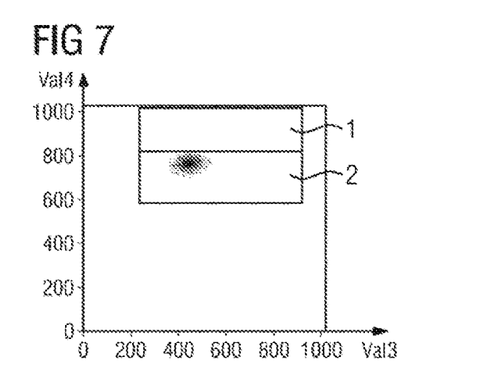
FIG. 7 shows characteristic scattering patterns for myeloblast and lymphoblast gates of an AML sample.

Sample of a patient with AML: a significant population in the 1$^{st}$ region:
>90% of all data points in the 1$^{st}$ region,
<10% of all data points in the 2$^{nd}$ region.

Figure 8:
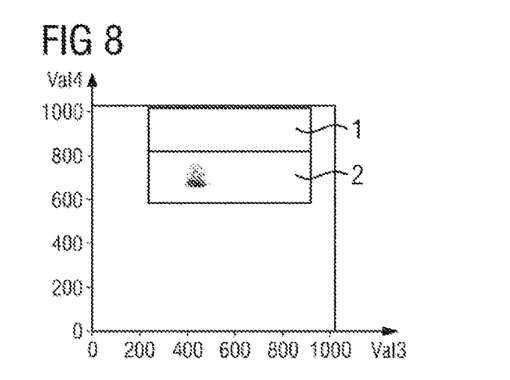
FIG. 8 shows characteristic scattering patterns for myeloblast and lymphoblast gates of a CML sample.

Sample of a patient with CML: a small number of data points in the 1$^{st}$ region:
>90% of all data points in the 1$^{st}$ region,
<10% of all data points in the 2$^{nd}$ region.

Figure 9:
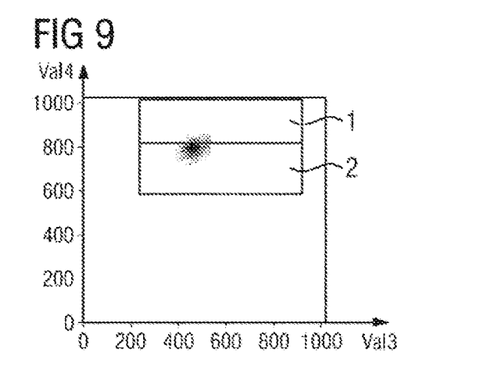
FIG. 9 shows characteristic scattering patterns for myeloblast and lymphoblast gates of an ALL sample.

Sample of a patient with ALL: a significant population extends over the 1$^{st}$ and 2$^{nd}$ region:
<90% of all data points in the 1$^{st}$ region,
>10% of all data points in the 2$^{nd}$ region.

Sample of a patient with CLL: a significant population in the 2$^{nd}$ region:
<10% of all data points in the 1$^{st}$ region,
>90% of all data points in the 2$^{nd}$ region.

Sample of a patient with OMF: a small number of data points in the 1$^{st}$ and 2$^{nd}$ region:
>80% of all data points in the 1$^{st}$ region,
<20% of all data points in the 2$^{nd}$ region.

In a third experimental example, there is the distinction between the 5 principal types of white blood cells and further sub-types without labeling.

Figure 13:
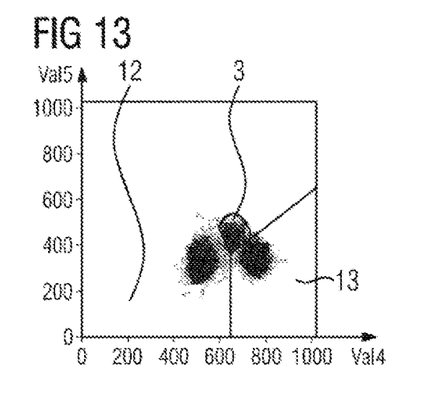
FIG. 13 shows distinguishing monocytes.

FIGS. 13 to 17 show the distinction between the 5 principal types of white blood cells and further sub-types without labeling, on the basis of characteristic scattering patterns in defined regions ("gates"). The abbreviation "E & N & IG" (12) represents eosinophils, neutrophils, and immature granulocytes (see FIG. 13). In this case, the immature granulocytes are metamyelocytes and myelocytes. The following regions are defined for distinguishing between the cell types (specified in each case are the use parameters and the X/Y-coordinates of the defined regions (gates)):

1$^{st}$ region="monocytes" gate (3): The monocyte cell type is distinguished as follows on account of the values of Val4 and Val5.

| Val4 | Val5 |
|---|---|
| 606 | 483 |
| 636 | 522 |
| 664 | 538 |
| 697 | 527 |
| 727 | 496 |
| 746 | 435 |

-continued

| Val4 | Val5 |
|---|---|
| 650 | 361 |
| 622 | 438 |

Figure 14:
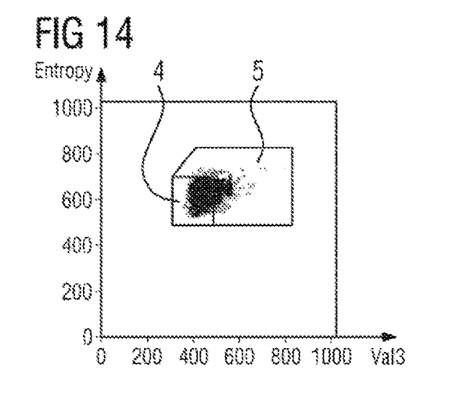
FIG. 14 shows distinguishing neutrophils and eosinophils.

2$^{nd}$ region="neutros" gate (4): The neutrophil cell type is distinguished as follows on account of the values of Val4 and Val5.

| Val4 | Val5 |
|---|---|
| 501 | 620 |
| 494 | 486 |
| 477 | 487 |
| 456 | 486 |
| 416 | 487 |
| 321 | 487 |
| 322 | 564 |
| 323 | 607 |
| 322 | 659 |
| 322 | 703 |
| 480 | 696 |

3$^{rd}$ region="eos" gate (5): The eosinophil cell type is distinguished as follows on account of the values of Val4 and entropy.

| Val4 | Entropy |
|---|---|
| 320 | 703 |
| 406 | 831 |
| 564 | 833 |
| 580 | 831 |
| 654 | 828 |
| 739 | 827 |
| 838 | 826 |
| 838 | 671 |
| 840 | 488 |
| 724 | 488 |
| 625 | 486 |
| 494 | 487 |
| 501 | 627 |
| 479 | 697 |

Figure 15:
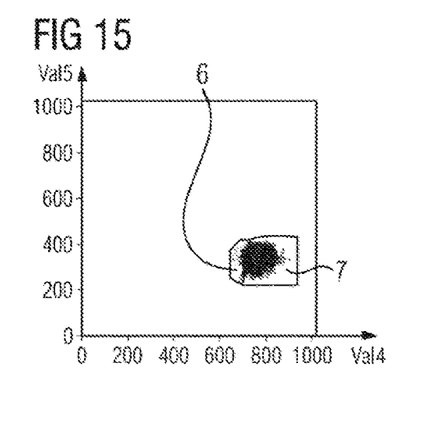
FIG. 15 shows distinguishing basophils and lymphocytes.

4$^{th}$ region="basos" gate (6): The basophil cell type is distinguished as follows on account of the values of Val4 and Val5.

| Val4 | Val5 |
|---|---|
| 732 | 422 |
| 717 | 347 |
| 699 | 222 |
| 643 | 254 |
| 645 | 386 |
| 683 | 415 |

5$^{th}$ region="lymphos" gate (7): The lymphocyte cell type is distinguished as follows on account of the values of Val4 and Val5.

| Val4 | Val5 |
|---|---|
| 781 | 438 |
| 826 | 436 |
| 936 | 426 |
| 937 | 223 |
| 861 | 223 |

| Val4 | Val5 |
| --- | --- |
| 801 | 218 |
| 698 | 212 |
| 717 | 347 |
| 731 | 424 |

Figure 16:
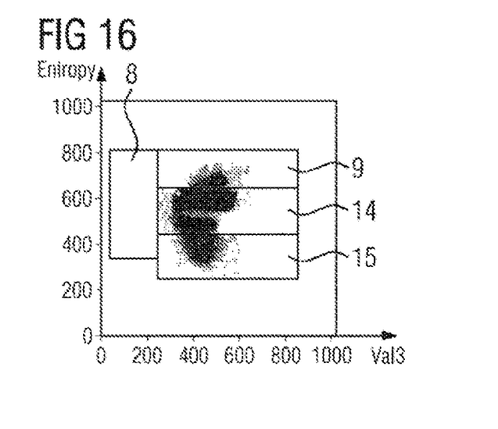
FIG. 16 shows distinguishing eosinophils, promyelocytes, blasts, and megakaryocytes.

6$^{th}$ region="megakaryocytes" gate (8): The megakaryocyte cell type is distinguished as follows on account of the values of Val3 and entropy.

| Val3 | Entropy |
| --- | --- |
| 33 | 233 |
| 332 | 805 |

7$^{th}$ region="promyelocytes" gate (9): The promyelocyte cell type is distinguished as follows on account of the values of Val3 and entropy.

| Val3 | Entropy |
| --- | --- |
| 233 | 846 |
| 642 | 805 |

Figure 17:
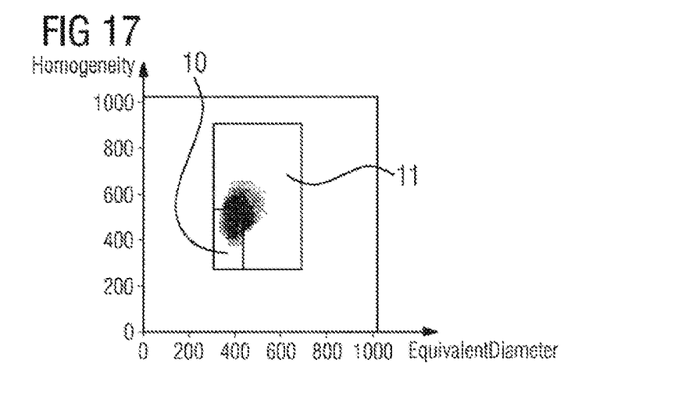
FIG. 17 shows distinguishing metamyelocytes on the basis of characteristic scattering patterns in defined regions ("gates"). PCA parameters (Val-X) or a combination of physical and PCA parameters are plotted in each case.

8$^{th}$ region="myelocytes" gate (10): The myelocyte cell type is distinguished as follows on account of the values of equivalentDiameter and homogeneity.

| EquivalentDiameter | Homogeneity |
| --- | --- |
| 333 | 534 |
| 304 | 534 |
| 304 | 493 |
| 304 | 436 |
| 304 | 272 |
| 367 | 273 |
| 429 | 274 |
| 427 | 408 |
| 427 | 470 |
| 418 | 524 |
| 400 | 532 |
| 377 | 534 |
| 356 | 534 |

9$^{th}$ region="metamyelocytes" gate (11): The metamyelocyte cell type is distinguished as follows on account of the values of equivalentDiameter and homogeneity.

| EquivalentDiameter | Homogeneity |
| --- | --- |
| 304 | 534 |
| 301 | 907 |
| 680 | 900 |
| 684 | 273 |
| 428 | 273 |
| 426 | 372 |
| 426 | 468 |
| 420 | 524 |
| 402 | 532 |
| 379 | 534 |

The invention claimed is:

1. An in-vitro method for determining a cell type of a white blood cell in a biological sample without labeling, the method comprising:
imaging the white blood cell using microscopy apparatus;
ascertaining physical parameters of the white blood cell from an image of the white blood cell by an automated image analysis; and
determining the cell type of the white blood cell based on the physical parameters and principal component analysis parameters, wherein the principal component analysis parameters comprise linear combinations of at least some of the physical parameters.

2. The method as claimed in claim 1, wherein a determined cell type of the white blood cell is a principal type of white blood cell selected from the group consisting of monocytes, neutrophils, basophils, eosinophils, and lymphocytes.

3. The method as claimed in claim 2, wherein the determined cell type is one of the principal types of white blood cells and a sub-type of white blood cells selected from the group consisting of myelocytes, metamyelocytes, promyelocytes, blasts, megakaryocytes, plasma cells, atypical lymphocytes, and Sézary cells.

4. The method as claimed in claim 1, wherein determination of a respective cell type of a multiplicity of white blood cells in a sample is used to characterize respective cell populations, and present cell populations are used to determine whether acute myeloid leukemia (AML), acute lymphoblastic leukemia (ALL), chronic myeloid leukemia (CML) or chronic lymphocytic leukemia (CLL) is present in a patient from whom the biological sample originated.

5. The method as claimed in claim 1, wherein the physical parameters of the cell comprise parameters selected from the group comprising area covered by the cell, perimeter of the cell, width of the cell, height of the cell, ratio of the width to the height of the cell, similarity of the geometric shape of the cell to a circle, mean radius of the cell, variance of the radius of the cell, degree of coverage of the cell, equivalent diameter corresponding to the covered area of the cell, optical volume of the cell, maximum optical height of the cell, minimum optical height of the cell, mean optical height of the cell, variance of the optical height of the cell, biconcavity of the cell, sphericity of the cell, shift of the center of mass of the cell, contrast of the cell, dissimilarity of the cell, homogeneity of the cell, energy of the cell, and entropy of the cell.

6. The method as claimed in claim 1, wherein imaging the white blood cell comprises overlaying a reference wave on an object wave, and recording a resultant interferogram or computer-implemented mathematical reconstruction.

7. The method as claimed in claim 1, wherein the microscopy apparatus is a microscope for performing digital holographic microscopy (DHM), interference phase microscopy, or quantitative phase microscopy.

8. The method as claimed in claim 1, wherein the white blood cells are imaged by the microscopy apparatus in a flow cell.

9. The method as claimed in claim 8, wherein the white blood cells are focused by laminar sheath flows.

10. The method as claimed in claim 1, further comprising removing red blood cells from the biological sample using selective lysis before the imaging of the white blood cell using the microscopy apparatus.

11. The method as claimed in claim 1, wherein the method is carried out using a non-stained or non-desiccated white blood cell.

12. The method as claimed in claim 1, wherein the method is performed using a whole blood sample or the biological sample contains blood cells, monocytes, neutrophils, basophils, eosinophils or lymphocytes.

13. The method as claimed in claim 8, wherein the flow cell comprises a channel with a rectangular or square cross-section.

14. The method as claimed in claim 9, wherein the white blood cells are focused by four laminar sheath flows.

* * * * *